US011759326B2

(12) United States Patent
Roche et al.

(10) Patent No.: US 11,759,326 B2
(45) Date of Patent: Sep. 19, 2023

(54) PLATFORM RTSA GLENOID PROSTHESIS WITH MODULAR ATTACHMENTS CAPABLE OF IMPROVING INITIAL FIXATION, FRACTURE RECONSTRUCTIONS, AND JOINT BIOMECHANICS

(71) Applicant: Exactech, Inc., Gainesville, FL (US)

(72) Inventors: Christopher P. Roche, Gainesville, FL (US); Matt Hamilton, Gainesville, FL (US); Phong Diep, Gainesville, FL (US); Tom Vanasse, Gainesville, FL (US); Corey Gaydos, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 0 days.

(21) Appl. No.: 16/320,892

(22) PCT Filed: Aug. 1, 2017

(86) PCT No.: PCT/US2017/044846
§ 371 (c)(1),
(2) Date: Jan. 25, 2019

(87) PCT Pub. No.: WO2018/026785
PCT Pub. Date: Feb. 8, 2018

(65) Prior Publication Data
US 2019/0159907 A1    May 30, 2019

Related U.S. Application Data

(60) Provisional application No. 62/369,519, filed on Aug. 1, 2016.

(51) Int. Cl.
*A61F 2/40*     (2006.01)
*A61B 17/86*    (2006.01)
(Continued)

(52) U.S. Cl.
CPC ............ *A61F 2/4081* (2013.01); *A61B 17/80* (2013.01); *A61B 17/86* (2013.01); *A61F 2002/30578* (2013.01); *A61F 2002/4085* (2013.01)

(58) Field of Classification Search
CPC .. A61F 2/40; A61F 2/4081; A61F 2002/4085; A61F 2002/285;
(Continued)

(56) References Cited

U.S. PATENT DOCUMENTS 7,959,680 B2 *  6/2011  Stone ................... A61F 2/4081
                                                      623/19.13
8,579,984 B2 * 11/2013  Borowsky ............. A61F 2/4684
                                                      623/19.14
(Continued)

FOREIGN PATENT DOCUMENTS

CN      111405882 A  *  7/2020  ......... A61F 2/30734
JP     2009-531085 A      9/2009
(Continued)

*Primary Examiner* — Bruce E Snow
(74) *Attorney, Agent, or Firm* — GREENBERG TRAURIG, LLP

(57) ABSTRACT

In some embodiments, the present invention provides a reverse shoulder glenoid prosthesis which supports the attachment of multiple different types of modular attachments that can: 1) provide additional scapular fixation (ie external to the glenoid) in order to improve glenoid implant fixation in cases of severe bone loss/fracture, 2) provide joint line lateralization to improve tissue stability in cases of severe glenoid/scapula bone loss, 3) facilitate use and containment of glenoid bone graft in cases of severe glenoid/scapula bone loss—particularly in those cases in which the glenoid defect is uncontained/peripheral 4) achieve glenoid fixation while at the same time reconstructing the scapular bone in cases of scapula fractures, glenoid fractures, and/or acromial fractures, and 5) provide improved rTSA joint (Continued)

biomechanics, particularly posterior rotator cuff efficiency by changing the line of action of the infraspinatus and teres minor muscles to improve their muscle tension, and also increase each muscle's external rotation and abduction moment arm lengths.

16 Claims, 16 Drawing Sheets

(51) Int. Cl.
*A61B 17/80* (2006.01)
*A61F 2/30* (2006.01)

(58) Field of Classification Search
CPC ...... A61F 2002/2417; A61F 2002/3417; A61F 2002/342
See application file for complete search history.

(56) References Cited

U.S. PATENT DOCUMENTS

| | | | |
|---|---|---|---|
| 9,089,430 B2* | 7/2015 | Pappas | A61F 2/30734 |
| 9,452,055 B2* | 9/2016 | Lappin | A61F 2/4603 |
| 9,629,725 B2* | 4/2017 | Gargac | A61F 2/4081 |
| 10,357,373 B2* | 7/2019 | Gargac | A61F 2/4081 |
| 10,383,735 B2* | 8/2019 | Wiley | A61F 2/40 |
| 10,980,640 B2* | 4/2021 | Chavarria | A61F 2/40 |
| 2007/0100458 A1* | 5/2007 | Dalla Pria | A61F 2/30721 623/19.13 |
| 2009/0281630 A1 | 11/2009 | Delince et al. | |
| 2010/0087924 A1 | 4/2010 | Roche et al. | |
| 2012/0209392 A1 | 8/2012 | Angibaud et al. | |
| 2013/0090737 A1* | 4/2013 | Flaherty | A61F 2/30749 623/19.13 |
| 2013/0261750 A1 | 10/2013 | Lappin | |
| 2013/0325131 A1* | 12/2013 | Roche | A61F 2/40 623/19.13 |
| 2016/0324649 A1* | 11/2016 | Hodorek | A61F 2/4081 |

FOREIGN PATENT DOCUMENTS

| | | |
|---|---|---|
| JP | 2014-511226 A | 5/2014 |
| WO | 2015/048385 A1 | 4/2015 |
| WO | 2016/069867 A | 5/2016 |

* cited by examiner

PLATFORM RTSA GLENOID PROSTHESIS WITH MODULAR ATTACHMENTS CAPABLE OF IMPROVING INITIAL FIXATION, FRACTURE RECONSTRUCTIONS, AND JOINT BIOMECHANICS

CROSS-REFERENCE TO RELATED APPLICATION

This application is a national phase filing under 35 USC 371 of International Application No. PCT/US2017/044846, filed on Aug. 1, 2017, entitled "PLATFORM RTSA GLENOID PROSTHESIS WITH MODULAR ATTACHMENTS CAPABLE OF IMPROVING INITIAL FIXATION, FRACTURE RECONSTRUCTIONS, AND JOINT BIOMECHANICS," which claims the benefit of commonly-owned, U.S. Provisional Patent Application No. 62/369,519, filed Aug. 1, 2016, entitled "PLATFORM RTSA GLENOID PROSTHESIS WITH MODULAR ATTACHMENTS CAPABLE OF IMPROVING INITIAL FIXATION, FRACTURE RECONSTRUCTIONS, AND JOINT BIOMECHANICS," the contents of which are incorporated by reference herein in their entirety.

TECHNICAL FIELD

Various embodiments of the present invention relate to an apparatus and method for reverse shoulder arthroplasty (rTSA). In particular, various embodiments of the present invention relate to an apparatus and method to achieve fixation, stability and function in the incidences of severe glenoid wear and glenoid/scapula fractures.

BACKGROUND

Short and mid-term clinical outcome studies have reported aseptic glenoid loosening rates between 0 and 12% with modern reverse shoulder arthroplasty (rTSA) designs. The potential factors influencing the rTSA glenoid loosening rate are numerous and include, but are not limited to: mechanical impingement, follow-up, bone quality, bone stock, initial fixation strength, and heightened patient demands. Because the reverse shoulder glenoid component is uncemented, aseptic glenoid loosening can occur due to insufficient initial fixation.

Similar challenges related to achieving initial glenoid fixation, joint stability, and function arise with glenoid, acromion, and/or scapula fractures. Achieving rTSA glenoid fixation in fractured glenoids or scapula is challenging as the surgeon must first reduce the fracture and compress and secure the fractured bone fragments together prior to compressing the rTSA prosthesis to the glenoid bone to achieve implant fixation.

SUMMARY OF INVENTION

In one embodiment, the present invention provides a reverse shoulder glenoid prosthesis which supports the attachment of multiple different types of modular attachments that can: 1) provide additional scapular fixation (ie external to the glenoid) in order to improve glenoid implant fixation in cases of severe bone loss/fracture, 2) provide joint line lateralization to improve tissue stability in cases of severe glenoid/scapula bone loss, 3) facilitate use and containment of glenoid bone graft in cases of severe glenoid/scapula bone loss—particularly in those cases in which the glenoid defect is uncontained/peripheral 4) achieve glenoid fixation while at the same time reconstructing the scapular bone in cases of scapula fractures, glenoid fractures, and/or acromial fractures, and 5) provide improved rTSA joint biomechanics, particularly posterior rotator cuff efficiency by changing the line of action of the infraspinatus and teres minor muscles to improve their muscle tension, and also increase each muscle's external rotation and abduction moment arm lengths.

In one embodiment, the modular attachment connects directly to the back of the glenosphere, or to the front of the glenoid baseplate, or to the back of the glenoid baseplate.

In one embodiment, the modular attachment provides additional scapular fixation, wherein the additional fixation is configured to improve implant fixation in a patient with severe bone loss and/or bone fracture.

In one embodiment, the modular attachment lateralizes the joint line, wherein the joint line lateralization is configured to improve tissue stability in a patient with severe bone loss and/or bone fracture.

In one embodiment, the modular attachment contains a glenoid bone graft in a patient with severe bone loss of the scapula and/or an uncontained glenoid defect.

In one embodiment, the modular attachment is configured to fixate the glenoid and restructure the scapular bone, in a patient with a scapular fracture, a glenoid fracture, and/or an acromial fracture.

In one embodiment, the modular attachment is a muscle augment configured to improve rTSA joint biomechanics in a patient in need thereof.

In some embodiments, a kit includes a prosthesis and a plurality of accessories, the prosthesis including a glenosphere, a glenoid plate, and a plurality of accessory fixation points, the glenosphere having a first side, a second side opposite the first side, an articular surface on the first side, a hollowed out portion on the second side, and a perimeter at an intersection of the first and second sides, the glenoid plate including a body portion and a stem portion, the body portion having a first side and a second side and being operatively connected to the hollowed out portion of the glenosphere such that the first side of the body portion faces the glenosphere, the stem portion extending from the second side of the body portion and being configured to be fixed to a glenoid of a patient, each of the plurality of accessory fixation points being configured to receive an accessory, each of the accessories being configured to be attached to a selected one of the accessory fixation points of the prosthesis.

In some embodiments, at least one of the plurality of accessories is configured to facilitate fixation of the prosthesis to the scapula. In some embodiments, at least one of the plurality of accessories has a first end that is configured to be attached to the selected one of the accessory fixation points of the prosthesis and a second end that is configured to be attached to the scapula. In some embodiments, the second end of the at least one of the plurality of accessories is configured to be attached to one of an anterior portion of the scapula, a posterior portion of the scapula, an acromion of the scapula, or a scapular spine. In some embodiments, the first end of the at least one of the plurality of accessories is configured to be attached to a selected two of the accessory fixation points of the prosthesis.

In some embodiments, at least one of the plurality of accessories has a shape corresponding to a shape of a portion of the scapula. In some embodiments, at least one of the plurality of accessories is one of contoured or bendable. In some embodiments, at least one of the plurality of accessories includes a bone augment. In some embodiments, the bone augment is configured to be positioned between the prosthesis and the scapula.

In some embodiments, at least one of the plurality of accessories includes a muscle augment. In some embodiments, the muscle augment is configured to translate a line of action so as to increase a moment arm of one of an infraspinatus muscle, a teres minor muscle, a subscapularis muscle, or a supraspinatus muscle.

In some embodiments, at least some of the fixation points are arrayed around the hollowed out portion on the second side of the glenosphere. In some embodiments, at least some of the fixation points extend through the glenoid plate from the first side of the body portion of the glenoid plate to the second side of the body portion of the glenoid plate. In some embodiments, a plurality of slots are formed in the second side of the glenosphere and extend from the perimeter to the hollowed-out portion so as to enable access to the fixation points at the second side of the body portion of the glenoid plate. In some embodiments, some of the fixation points are arrayed around the hollowed out portion on the second side of the glenosphere, and wherein some of the fixation points extend through the glenoid plate from the first side of the body portion of the glenoid plate to the second side of the body portion of the glenoid plate.

In some embodiments, a prosthesis includes a glenosphere, a glenoid plate, and a plurality of accessory fixation points, the glenosphere having a first side, a second side opposite the first side, an articular surface on the first side, a hollowed out portion on the second side, and a perimeter at an intersection of the first and second sides, the glenoid plate including a body portion and a stem portion, the body portion having a first side and a second side and being operatively connected to the hollowed out portion of the glenosphere such that the first side of the body portion faces the glenosphere, the stem portion extending from the second side of the body portion and being configured to be fixed to a glenoid of a patient, each of the plurality of accessory fixation points being configured to receive an accessory.

In some embodiments, at least some of the fixation points are arrayed around the hollowed out portion on the second side of the glenosphere. In some embodiments, at least some of the fixation points extend through the glenoid plate from the first side of the body portion of the glenoid plate to the second side of the body portion of the glenoid plate. In some embodiments, a plurality of slots are formed in the second side of the glenosphere and extend from the perimeter to the hollowed-out portion so as to enable access to the fixation points at the second side of the body portion of the glenoid plate. In some embodiments, some of the fixation points are arrayed around the hollowed out portion on the second side of the glenosphere, and wherein some of the fixation points extend through the glenoid plate from the first side of the body portion of the glenoid plate to the second side of the body portion of the glenoid plate.

BRIEF DESCRIPTION OF DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

Figure 1:
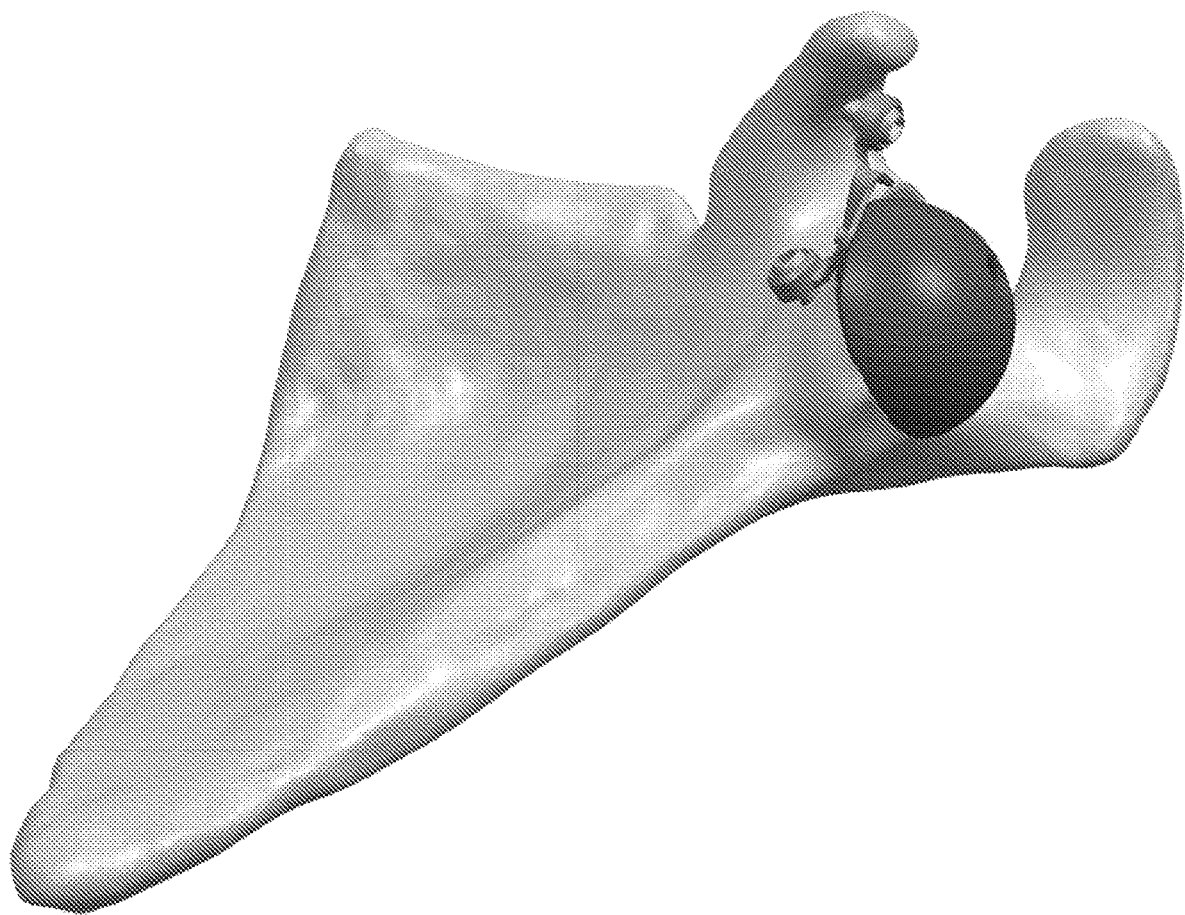
FIG. 1 shows a modular attachment according to some aspects of the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

DESCRIPTION OF EXEMPLARY EMBODIMENTS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, throughout the specification, the meaning of "a," "an," and "the" include plural references. The meaning of "in" includes "in" and "on."

In some embodiments, the present invention provides a reverse shoulder glenoid prosthesis which supports the attachment of multiple different types of modular attachments that can: 1) provide additional scapular fixation (ie external to the glenoid) in order to improve glenoid implant fixation in cases of severe bone loss/fracture, 2) provide joint line lateralization to improve tissue stability in cases of severe glenoid/scapula bone loss, 3) facilitate use and containment of glenoid bone graft in cases of severe glenoid/scapula bone loss—particularly in those cases in which the glenoid defect is uncontained/peripheral 4) achieve glenoid fixation while at the same time reconstructing the scapular bone in cases of scapula fractures, glenoid fractures, and/or acromial fractures, and 5) provide improved rTSA joint biomechanics, particularly posterior rotator cuff efficiency by changing the line of action of the infraspinatus and teres minor muscles to improve their muscle tension, and also increase each muscle's external rotation and abduction moment arm lengths.

In some embodiments, the modular attachment connects directly to the back of the glenosphere, or to the front of the glenoid baseplate, or to the back of the glenoid baseplate.

In some embodiments, the modular attachment includes posts, screws (locking/compression/or poly-axial locking), fins, and or cables/sutures at various angles and positions configured to facilitate attachment of the modular attachments to the patient's bone.

In some embodiments, the modular attachment may be used without attachment to a rTSA prosthesis. Specifically, the modular attachment may be attached to an rTSA prosthesis or be used without a prosthesis, where the the modular attachment is connected directly to the bone. Such modular attachments may be used in the humerus of the shoulder joint or in other joints for similar applications, as well as a revision arthroplasty platform.

The modular attachments can be be manufactured from different biocompatible materials, including, for example, Co—Cr, stainless steel, titanium, carbon fiber, ceramic, PMMA bone cement, pyrocarbon, and/or bone graft. Furthermore, the modular attachments can be fabricated by traditional computer added manufacturing processes, or by using additive manufacturing or similar processes.

The modular attachments can be surface coated or treated with various processes to encourage fixation to the muscle and/or bone.

Modular rTSA Glenoid Attachments to Provide Additional Scapular Fixation in Order to Improve Implant Fixation in Cases of Severe Bone Loss and/or Bone Fracture According to Some Embodiments of the Present Invention In some embodiments, the modular attachment provides additional scapular fixation, wherein the additional fixation is configured to improve implant fixation in a patient with severe bone loss and/or bone fracture.

Referring to FIGS. 1-8, depicted are multiple modular contoured plates which correspond to the anatomic shape of various regions of the scapula. In some embodiments, these modular plates accept one or more locking, compression, or compression locking screws (and/or other fixation devices, such as sutures or wires) and can secure to the back of the glenosphere, or to the back or front of the baseplate, in order to facilitate additional scapula fixation (i.e. external to the glenoid) for clinical situations in which there is insufficient bone behind the rTSA baseplate to achieve fixation.

It should be noted that the method of modular attachment of these devices to the glenosphere or glenoid baseplate can vary and can include tapers, clips, screws, or other clasping mechanisms to secure the modular devices.

To provide additional patient-specific functionality or improved function in abnormal scapula morphologies, the modular plates can be designed so that they are bendable either fully or at pre-defined regions so that the surgeon can shape the plate intra-operatively to meet the specific anatomic/morphological needs of a particular patient during surgery. Conversely, the plates can be provided fully-machined and contoured in multiple sizes to fit multiple different anatomies.

In some embodiments, the modular attachments can also be used to help reconstruct scapula fractures at the time of the rTSA surgery, be it the primary surgery or in a revision after occurrence of a boney fracture. The modular attachments can be secured in 360° around the glenosphere or glenoid baseplate, as is required by the particular patient's anatomy or fracture type/location. Additionally, depicted below are multiple positions of these modular attachments which support multiple additional locations for screw fixation in the scapula to facilitate additional implant fixation.

FIG. 1 shows an oblique view of a contoured and/or bendable frame that accepts screws and secures to one of the back or front of the baseplate, or to the back of the glenosphere to facilitate additional scapula fixation. Depicted in FIG. 1 is an embodiment in which a plate is modularly connected to the back of the glenosphere to position and orient multiple screws to the anterior scapula.

Figure 2:
FIG. 2 shows another view of a modular attachment according to some aspects of the present invention.

FIG. 2 shows a front view of a contoured and/or bendable frame that accepts screws and secures to one of the back or front of the baseplate, or to the back of the glenosphere to facilitate additional scapula fixation. Depicted in FIG. 2 is an embodiment in which a plate is modularly connected to the back of the glenosphere to position and orient multiple screws to the anterior scapula.

Figure 3:
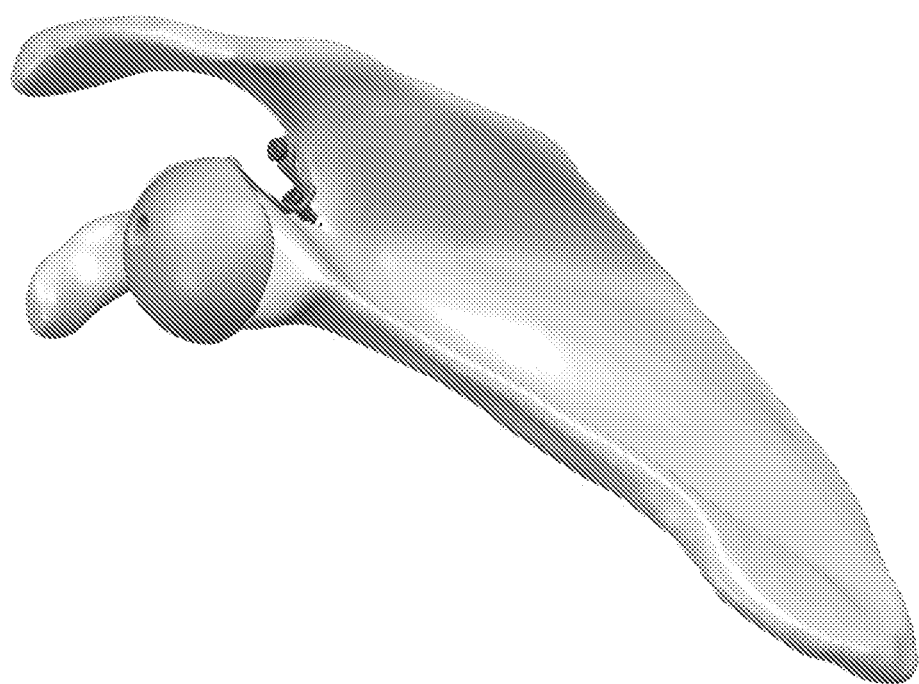
FIG. 3 shows another view of a modular attachment according to some aspects of the present invention.

FIG. 3 shows an oblique view of a contoured and/or bendable frame that accepts screws and secures to one of the back or front of the baseplate, or to the back of the glenosphere to facilitate additional scapula fixation. Depicted in FIG. 3 is an embodiment in which a plate is modularly connected to the back of the glenosphere to position and orient multiple screws to the posterior scapula/base of the acromion.

Figure 4:
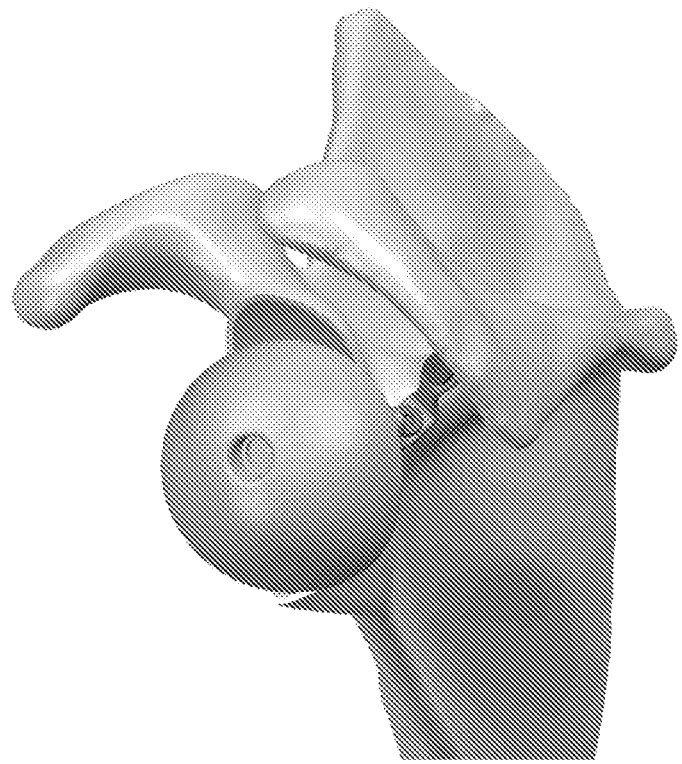
FIG. 4 shows another view of a modular attachment according to some aspects of the present invention.

FIG. 4 shows an alternate view of a contoured and/or bendable frame that accepts screws and secures to one of the back or front of the baseplate, or to the back of the glenosphere to facilitate additional scapula fixation. Depicted in FIG. 4 is an embodiment in which a plate is modularly connected to the back of the glenosphere to position and orient multiple screws to the posterior scapula/base of the acromion.

Figure 5:
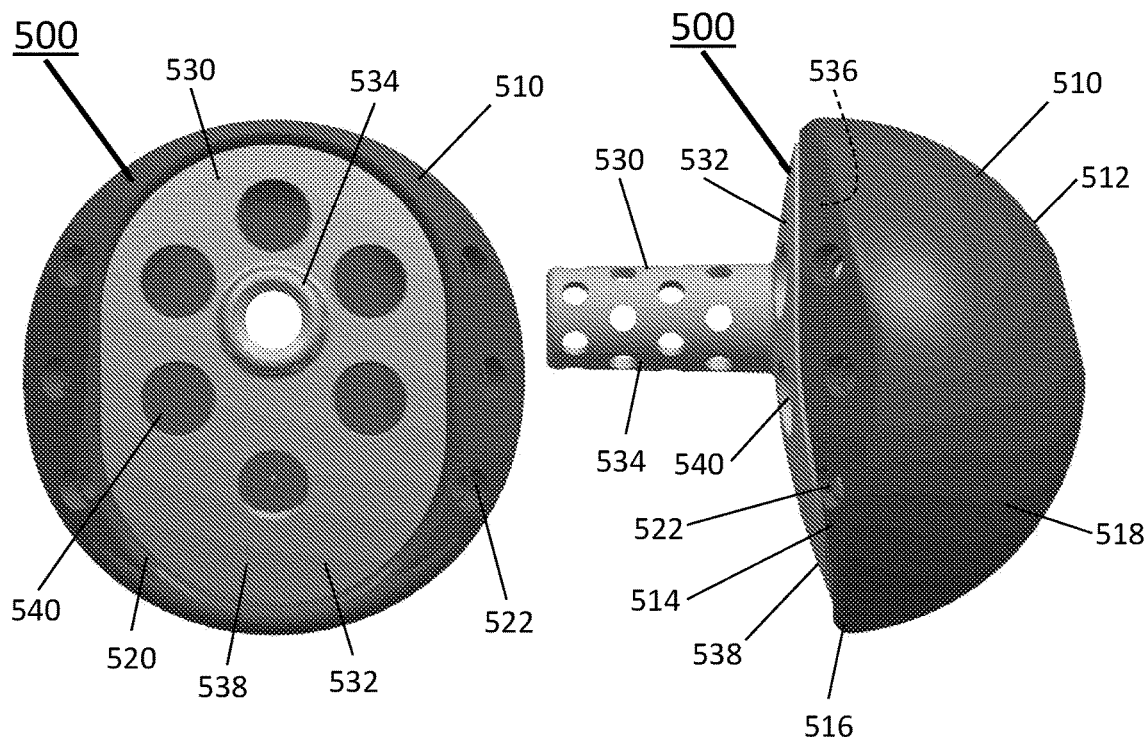
FIG. 5 shows a glenoshphere according to some aspects of the present invention.

FIG. 5 shows medial and anterior views a prosthesis 500 configured to attach a modular attachment according to some embodiments of the present invention. The prosthesis 500 includes a glenosphere 510 and a glenoid baseplate 530. The glenosphere 510 has a first side 512, a second side 514 opposite the first side 512, and a perimeter 516 where the first side 512 meets the second side 514. An articular surface 518 is formed on the first side 512 of the glenosphere 510. The articular surface 512 is configured to engage a cup portion fixed to a resected humerus. A hollowed-out portion 520 is formed in the second side 514 of the glenosphere 510. A plurality of attachment points 522 are arrayed around the hollowed-out portion 520 proximate the perimeter 516.

Continuing to refer to FIG. 5, The glenoid baseplate 530 includes a body portion 532 and a stem portion 534. The body portion 532 is positioned within the hollowed-out portion 520 of the glenosphere 510. In some embodiments, the body portion 532 is fixed within the hollowed-out portion 520 of the glenosphere 510. In some embodiments, the body portion 532 is removably positioned within the hollowed-out portion 520 of the glenosphere 510. The body portion 532 has a first side 536 and a second side 538 opposite the first side 536. The first side 536 faces the glenosphere 510 and the second side 538 faces away from the glenosphere 510. In some embodiments, the first side 536 is substantially planar. In some embodiments, the second side 538 is convex. The stem portion 534 extends from the second side 538 and is configured to be fixed to a glenoid of a patient. A plurality of attachment points 540 are arrayed around the stem portion 534 and extend through the body portion 532 from the first side 536 to the second side 538. The attachments can be attached at multiple different positions, 360° around the glenosphere to position the fixation devices at various locations and orientations.

Figure 6:
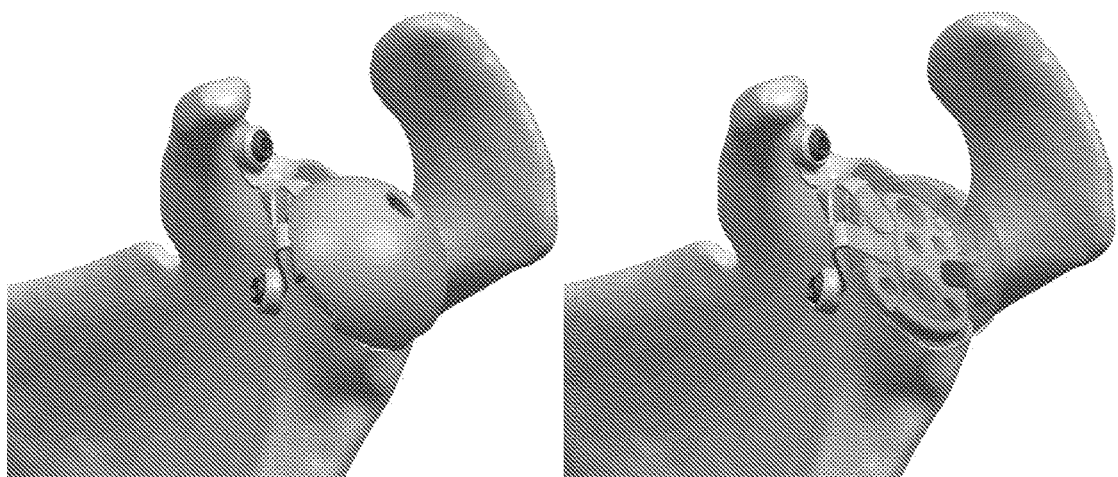
FIG. 6 shows a modular attachment according to some aspects of the present invention.

FIG. 6 shows an alternative embodiment of a contoured and/or bendable frame that accepts multiple screws and secures to the baseplate to position and orient multiple screws to the anterior scapula. Note that the glenosphere articulation is cut-out in a non-articulating surface so not to limit prosthesis range of motion or create prosthesis impingement, which could lead to instability.

Figure 7:
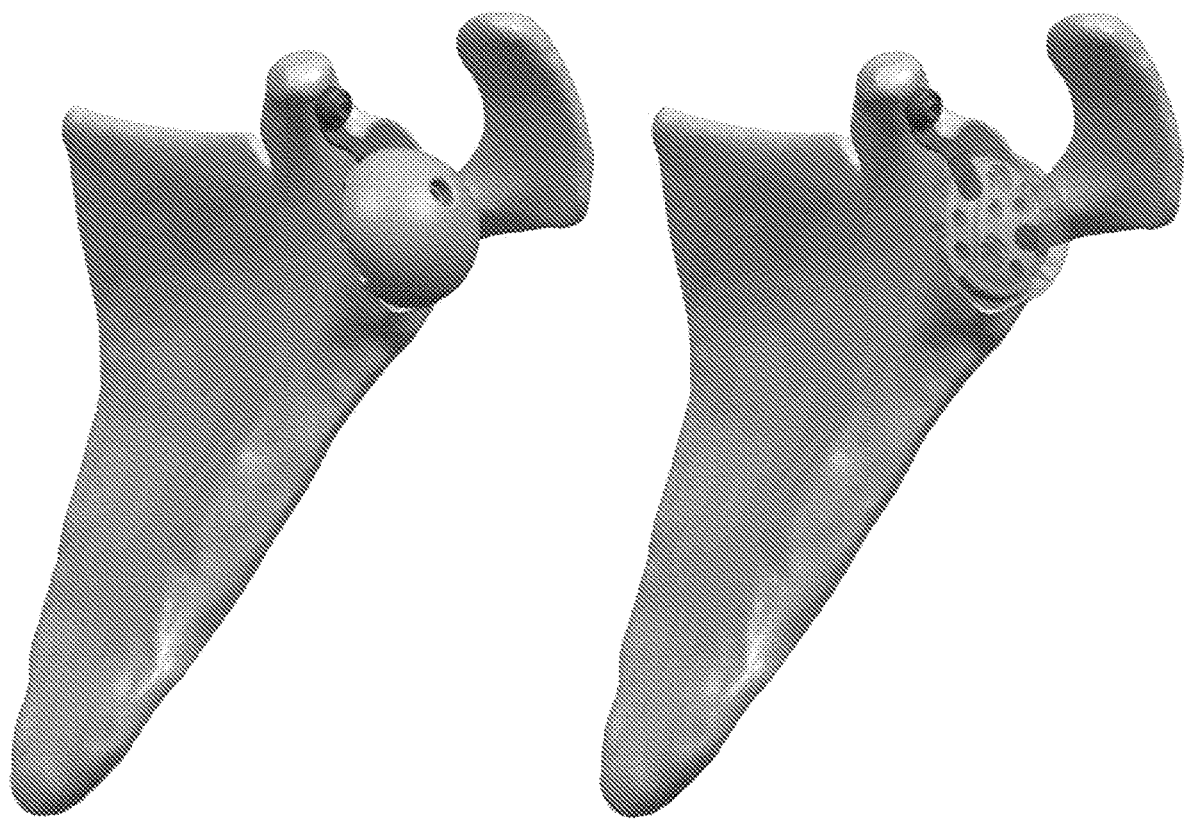
FIG. 7 shows a modular attachment according to some aspects of the present invention.

FIG. 7 shows an alternative embodiment of a contoured and/or bendable frame that accepts a single screw and secures to the baseplate to position and orient the screws to the anterior scapula.

Figure 8:
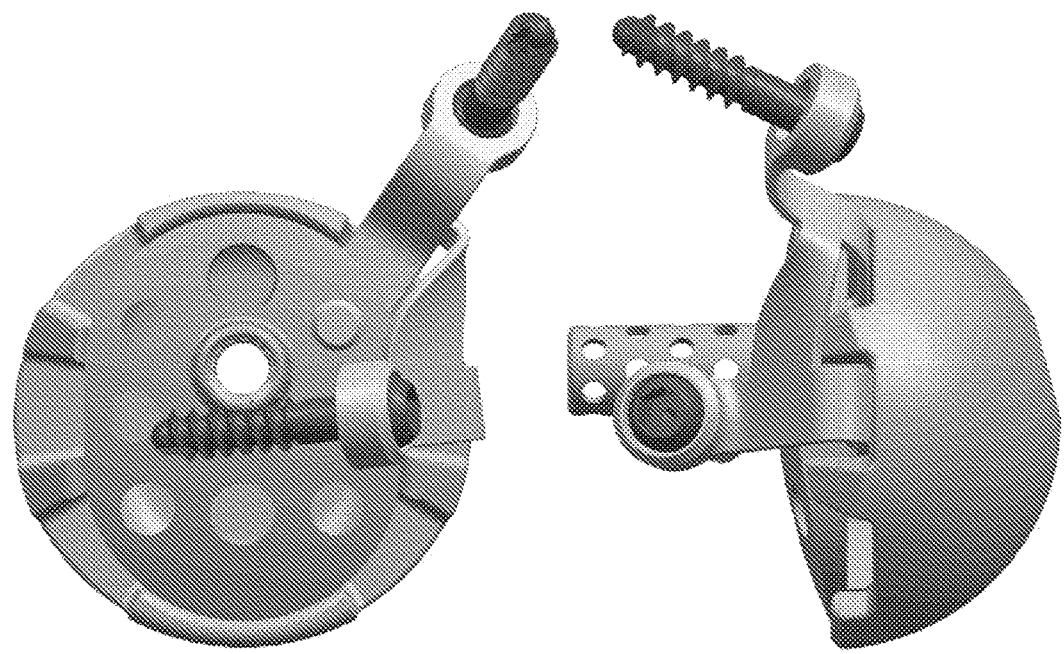
FIG. 8 shows a modular attachment according to some aspects of the present invention.

FIG. 8 shows how different modular fixation devices can be secured in multiple positions, 360° around the baseplates to position screws at various locations and orient the screws at multiple angles. In some embodiments, slots are formed about the perimeter of the glenosphere so as to enable modular fixation devices to be fixed to the side of the baseplate that faces the glenosphere.

Modular rTSA Glenoid Bone Augment Attachments to Provide Joint Line Lateralization to Improve Tissue Stability in Cases of Severe Glenoid/Scapula Bone Loss According to Some Embodiments of the Present Invention In some embodiments, the modular attachment lateralizes the joint line (i.e., translates the joint line in a lateral direction). In some embodiments, the joint line lateralization is configured to improve tissue stability in a patient with severe bone loss and/or bone fracture.

FIGS. 9 to 12 depict multiple modular bone augments which attach to the back of the baseplate to increase the implant surface contact area with the deformed or fractured bone, in order to improve its fixation and increase its options for screw/fixation attachment.

In some embodiments, the modular bone augments are provided in various shapes, sizes, and thicknesses (which could be either uniform or nonuniform—i.e. wedges or cones, to account for the multiple different types of glenoid/scapula defects: posterior, superior, medial, or combined defects, including contained or uncontained/peripheral defects.

In some embodiments, the modular bone augments accept locking, compression, or compression locking screws (and/or other fixation devices, such as sutures or wires) so that it can be secured directly to deformed or fractured scapula and/or the bone augments could have thru-holes so that it can permit locking, compression, or compression locking screws (and/or other fixation devices, such as sutures or wires) to be passed through the augment as those screws/fixation devices are secured directly to the baseplate. Additionally, the bone augment may be modularly attached to the baseplate using various methods, including tapers, clips, screws, or other clasping mechanisms to secure the augment to the baseplate. Alternatively, the bone augment could attach to the front of the baseplate or to the back of the glenosphere.

In some embodiments, augments are configured to fill large nerot-sirveaux scapula notch defects. In some embodiments, the augments are secured via a boot strap method, in which a scapular neck wedge augment is secured into the scapular notch and secured to the host bone with screws and modularlly connected to one of the baseplate or glenosphere via a modular connection.

Figure 9:
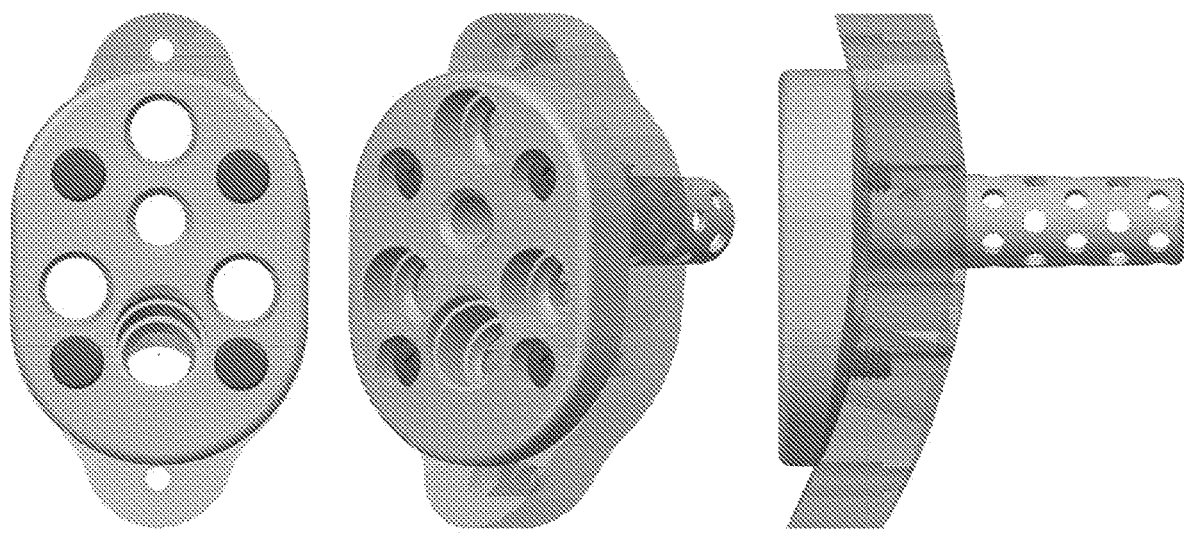
FIG. 9 shows a modular attachment according to some aspects of the present invention.
Figure 10:
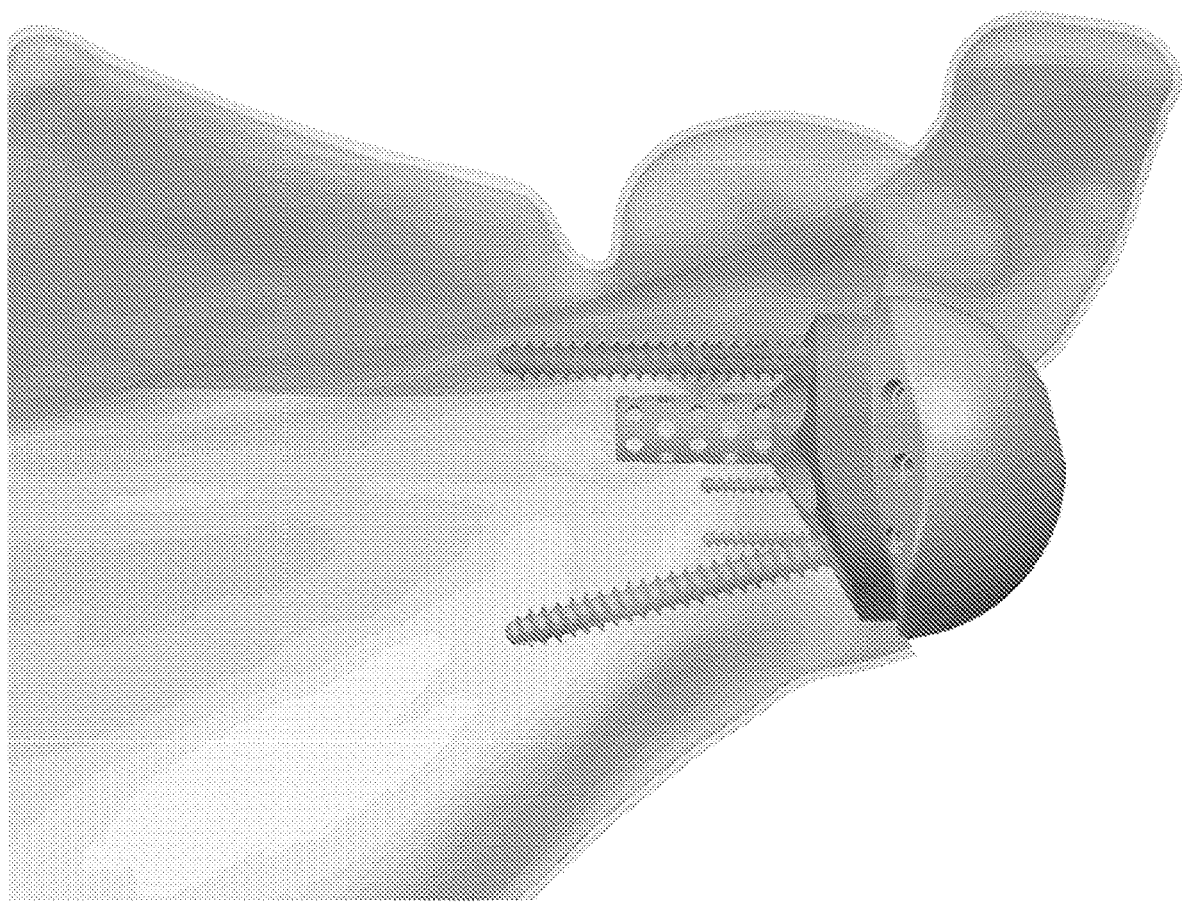
FIG. 10 shows another view of a modular attachment according to some aspects of the present invention.
Figure 11:
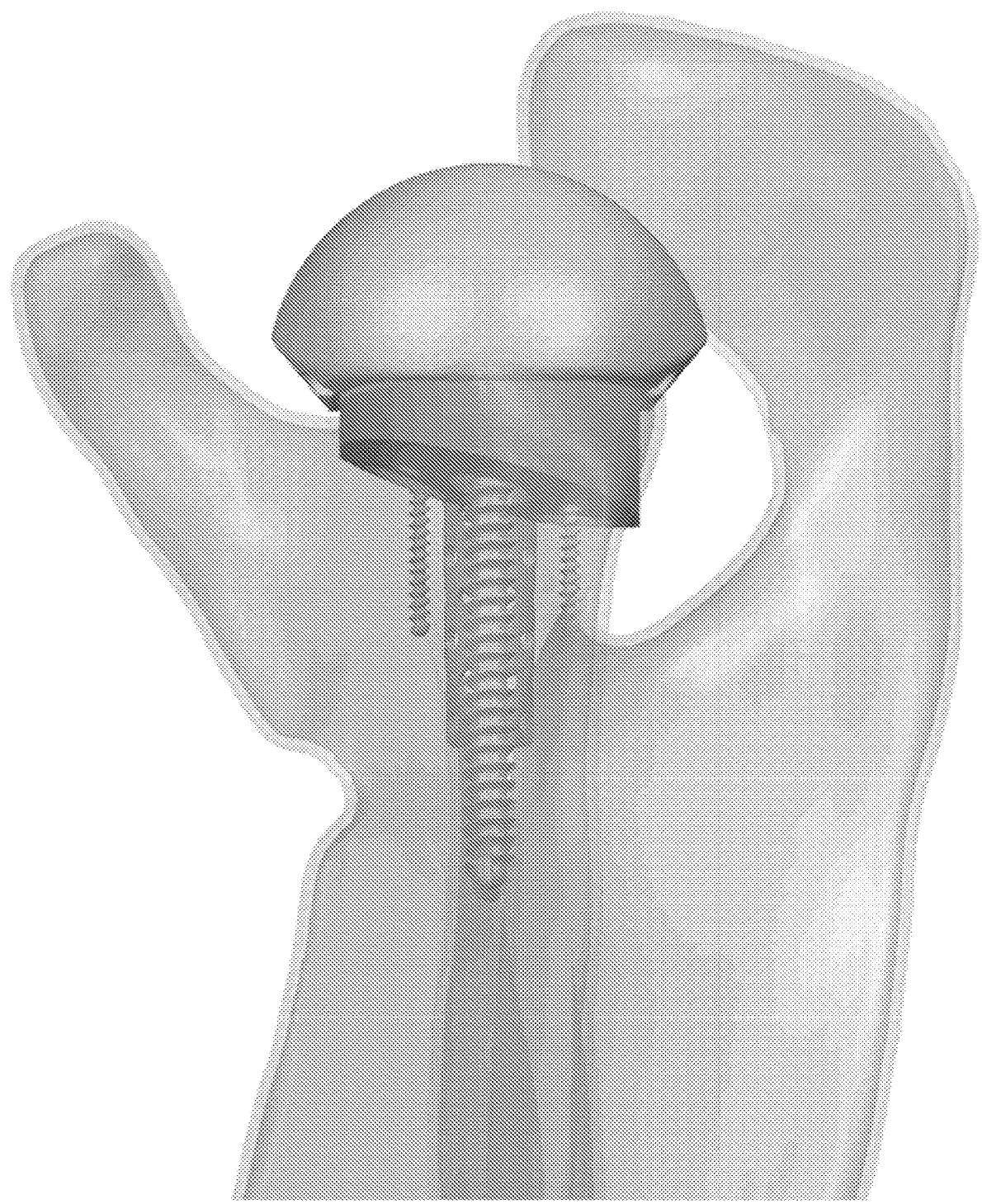
FIG. 11 shows another view of a modular attachment according to some aspects of the present invention.
Figure 12:
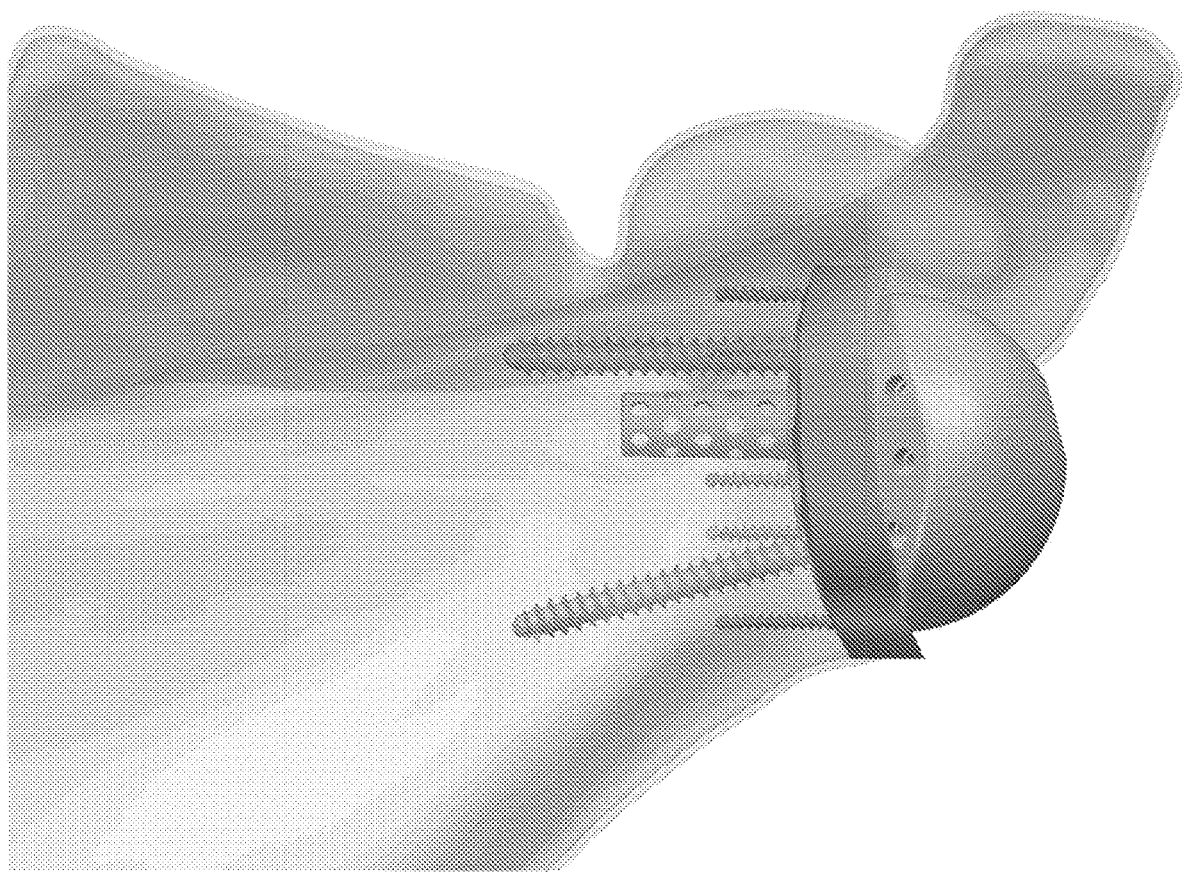
FIG. 12 shows another view of a modular attachment according to some aspects of the present invention.

FIG. 9 shows one embodiment of a modular bone augment that accepts screws and secures to the back of the baseplate to improve surface contact area with the deformed or fractured scapula and provide additional location options for fixation. FIGS. 10-12 show examples of multiple different shapes, sizes, and thicknesses of bone augments that can be fabricated in either of uniform or nonuniform thickness, for example wedges or cones, to account for the multiple different types of defects: posterior, superior, medial, or combined defects, including contained or uncontained/peripheral defects. FIG. 10 shows a conical augment. FIG. 11 shows a posterior augment wedge. FIG. 12 shows a lateral augment.

Modular rTSA Glenoid Attachments to Facilitate Use and Containment of Glenoid Bone Graft in Cases of Severe Glenoid/Scapula Bone Loss—Particularly in Those Cases in Which the Glenoid Defect is Uncontained/Peripheral According to Some Embodiments of the Present Invention In one embodiment, the modular attachment contains a glenoid bone graft in a patient with severe bone loss of the scapula and/or glenoid.

FIGS. 13 to 16 show multiple modular contoured plates which correspond to the anatomic shape of the anterior and posterior external glenoid/scapula cortical. These modular plates can modularly connect to the back of the glenosphere or to or to the back or front of the baseplate, and are intended to aid a surgeon in reconstructing an uncontained/peripheral glenoid defect using bone graft.

Generally uncontained/peripheral glenoid defects are unable to be grafted due to graft displacement; however, this design concept facilitates grafting an uncontained/peripheral defect in such a clinical scenario by creating a physical block to contain it and also provide additional locations for supplemental fixation to the graft/host bone.

In some embodiments, the plates may be used to cover the scapular notch in revisions, if patients have a large nerotsirveaux scapular notch in order to bridge the notch (which functions like an uncontained defect) to strengthen the scapula. In some embodiments, a U-shaped plate could also be used to contain bone graft should a surgeon want to graft the notched scapula.

It should be noted that the method of modular attachment of these contoured plates to the glenosphere or glenoid baseplate can vary and can include tapers, clips, screws, or other clasping mechanisms to secure the modular devices.

In some embodiments, to provide additional patient-specific functionality or improved function in abnormal scapula morphologies, the modular plates can be designed so that they are bendable either fully or at pre-defined regions so that the surgeon can shape the plate intra-operatively to meet the specific anatomic/morphological needs of a particular patient during surgery.

Figure 13:
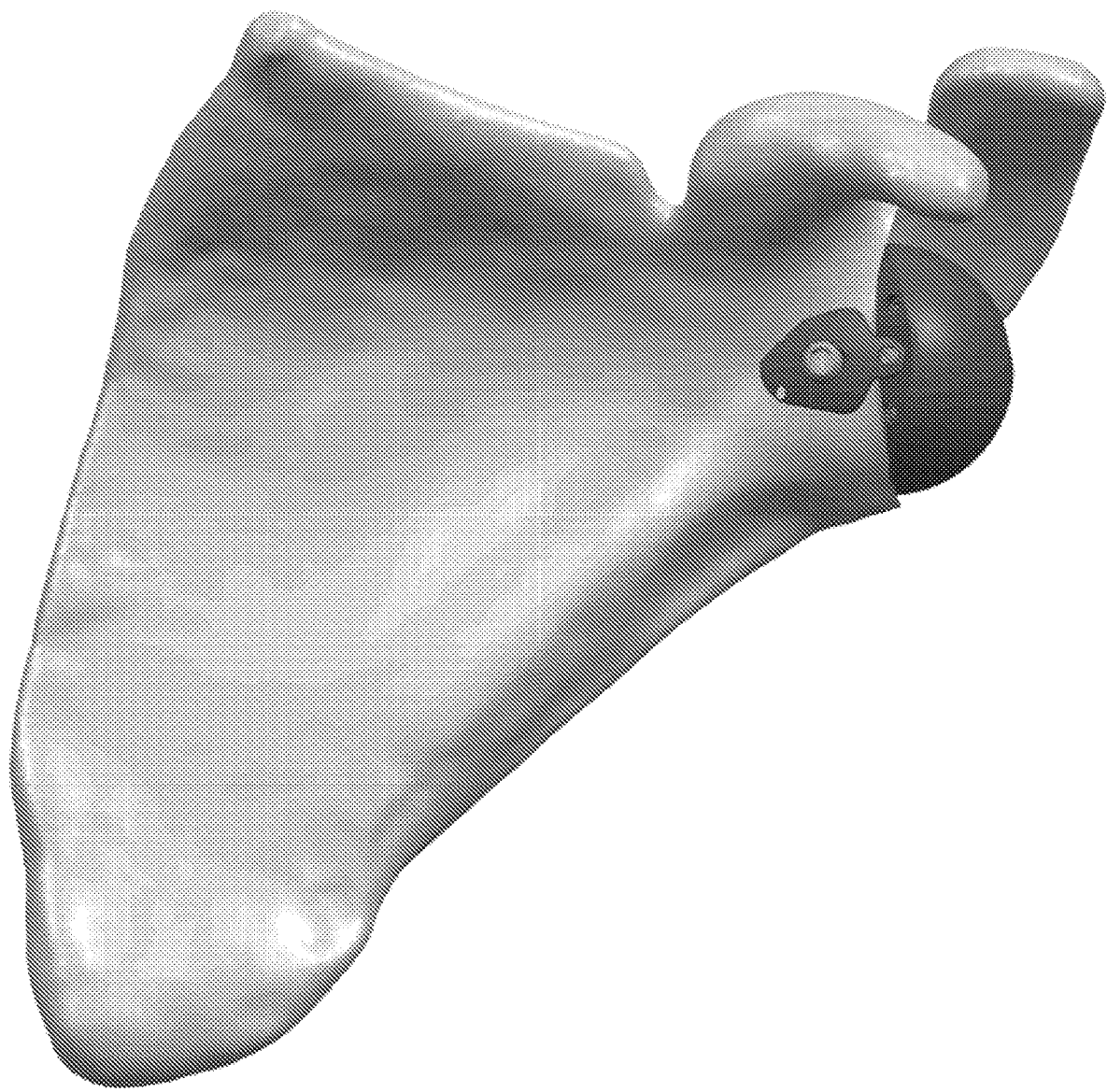
FIG. 13 shows a modular attachment according to some aspects of the present invention.
Figure 14:
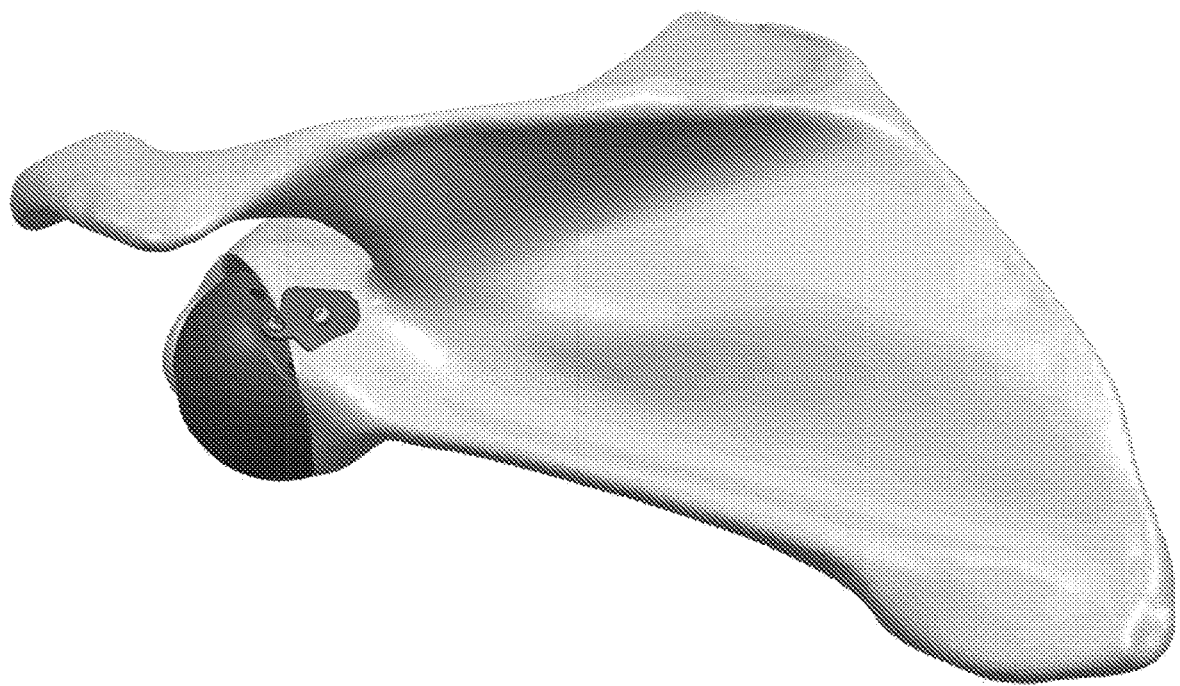
FIG. 14 shows another view of a modular attachment according to some aspects of the present invention.
Figure 15:
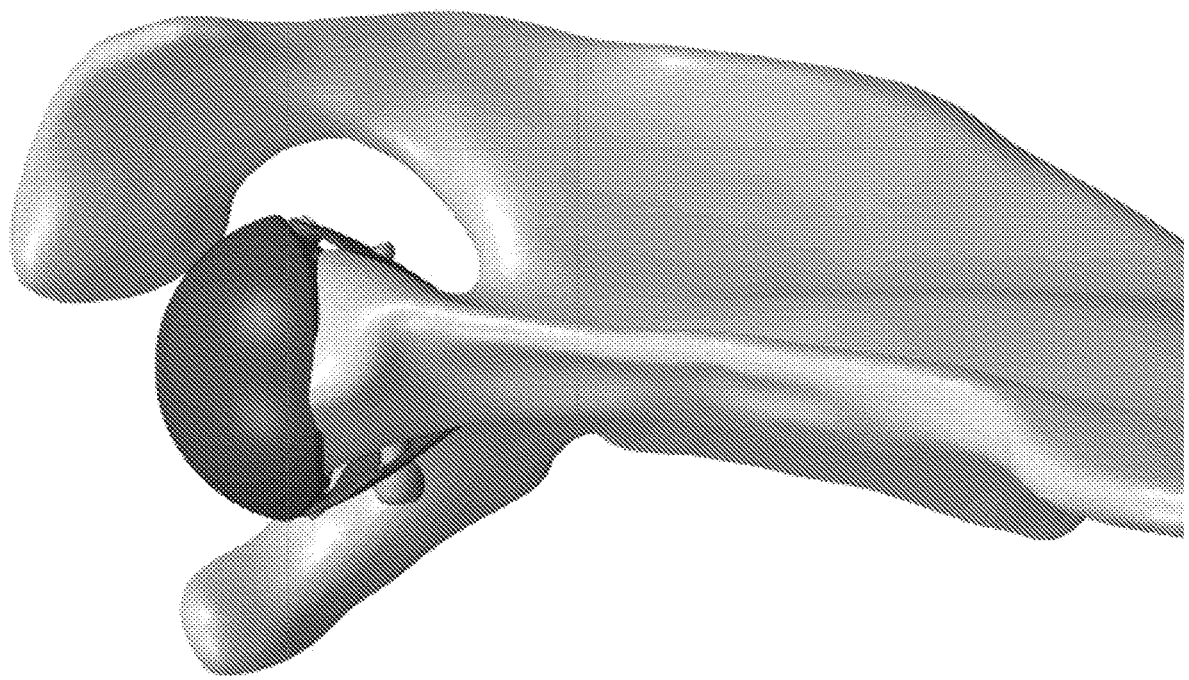
FIG. 15 shows another view of a modular attachment according to some aspects of the present invention.

FIGS. 13 to 15 show an embodiment of a modular contoured or bendable plate that secures to the rTSA glenoid component to contain and facilitate glenoid bone grafting in scapula with peripheral defects. FIG. 13 shows such a plate on the anterior scapula. FIG. 14 shows such a plate on the posterior scapula.

In some embodiments, a modular contoured or bendable plate can be secured all around the glenoid component. FIG. 15 shows modular contoured or bendable plates secured to the anterior scapula and to the posterior scapula to describe the most common locations of peripheral glenoid defects.

Figure 16:
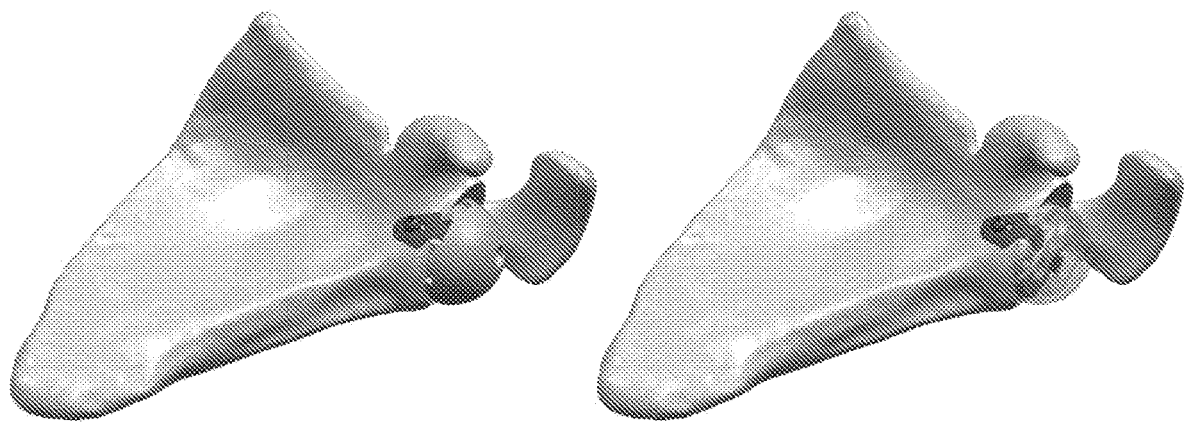
FIG. 16 shows another view of a modular attachment according to some aspects of the present invention.

FIG. 16 shows an alternate embodiment of design in which the contoured or bendable plate modularly connects to the baseplate instead of the glenosphere.

Modular rTSA Glenoid Attachments to Achieve Glenoid Fixation While at the Same Time Reconstructing the Scapular Bone in Cases of Scapula Fractures, Glenoid Fractures, and/or Acromial Fractures According to Some Embodiments of the Present Invention In one embodiment, the modular attachment is configured to fixate the glenoid and restructure the scapular bone, in a patient with a scapular fracture, a glenoid fracture, and/or an acromial fracture.

Figure 17:
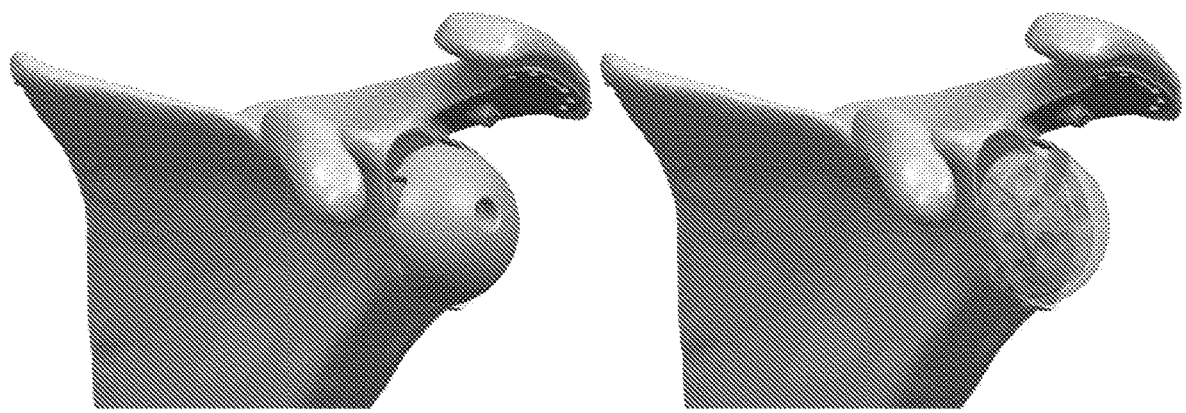
FIG. 17 shows a modular attachment according to some aspects of the present invention.
Figure 18:
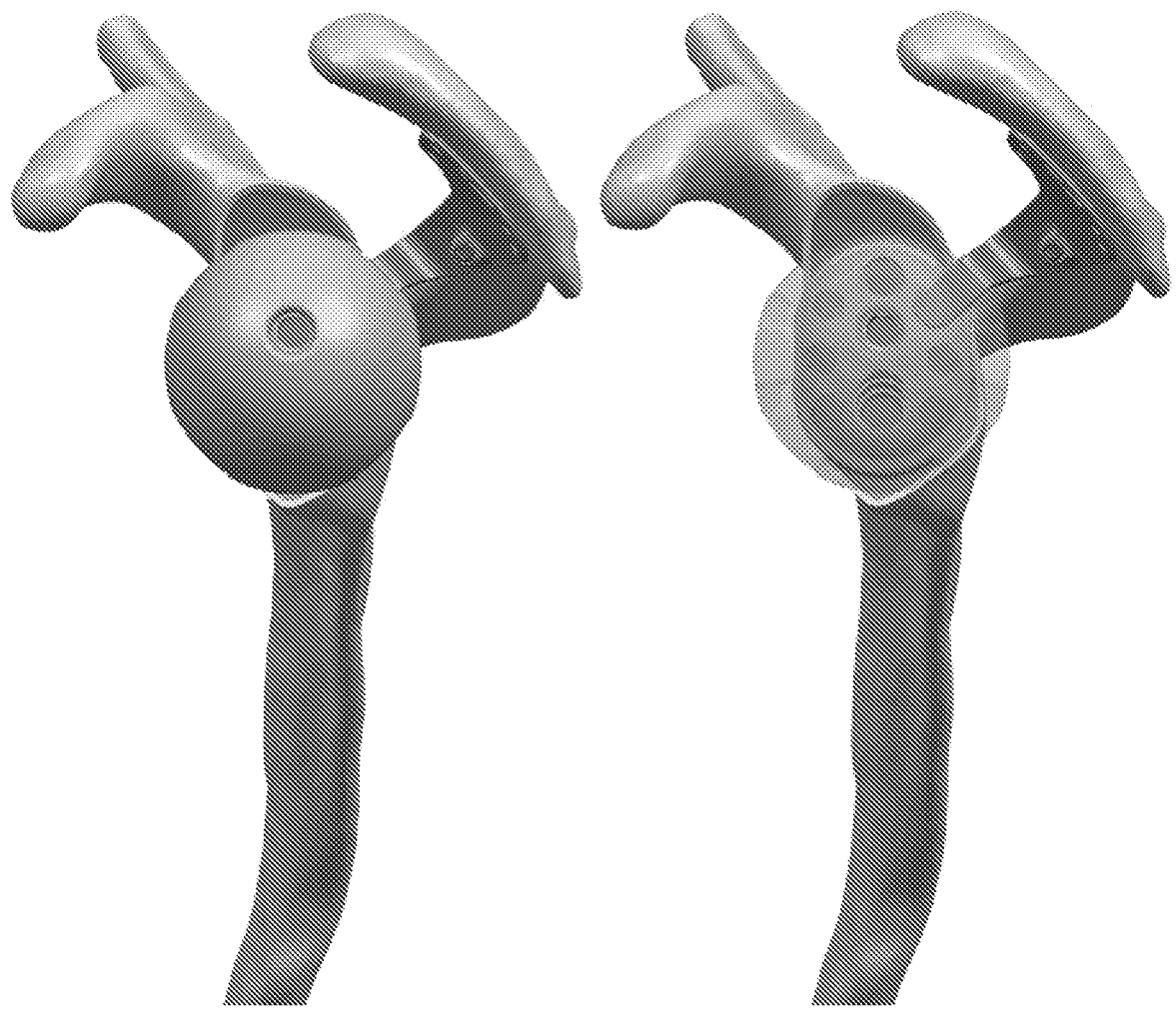
FIG. 18 shows another view of a modular attachment according to some aspects of the present invention.
Figure 19:
FIG. 19 shows another view of a modular attachment according to some aspects of the present invention.

FIGS. 17 to 19 show multiple modular fracture plates which correspond to the anatomic shape of various regions of the scapula.

In some embodiments, the modular fracture plates accept one or more locking, compression, or compression locking screws (and/or other fixation devices, such as sutures or wires) and can secure to the back of the glenosphere, or to the back or front of the baseplate, in order to facilitate additional scapula fixation for clinical situations in which there is a need to reconstruct a fractured scapula while also achieving implant fixation. Note that the fracture plate depicted in FIGS. 17 to 19 is specifically for acromial fractures as they are a common rTSA complication, but other fracture plates that are contoured to fit the scapula can be used. Additionally, for the acromial fracture plate, note that the plate is very low profile so that it doesn't create any prosthesis impingement, which would like ROM and potentially lead to instability. Additionally, note that the acromial plate is positioned under the acromion to provide additional support and buttress the fracture to improve the reconstruction. It is important to note that such an acromial fracture plate may also be used preventively/prophylactically at the time of the initial rTSA surgery in order to provide additional acromial stiffness to reduce the load the acromion experiences and in turn limit the probability of acromial fatigue fractures, a common rTSA complication. Regardless of the type of modular fracture plate used, it should be noted that the method of modular attachment of these fracture plates to the glenosphere or glenoid baseplate can vary and can include tapers, clips, screws, or other clasping mechanisms to secure the modular devices. To provide additional patient-specific functionality or improved function in abnormal scapula morphologies, these modular fracture plates can be designed so that they are bendable either fully or at pre-defined regions so that the surgeon can shape the plate intra-operatively to meet the specific anatomic/morphological needs of a particular patient during surgery. In some embodiments, the acromial plate is configured to be attached to the underside of the acromion. In some embodiments, the acromial plate is configured to be attached to the lateral side of the acromion. In some embodiments, a modular fracture plate is configured to be attached to the scapular spine.

In some embodiments, the modular devices can be secured in 360° around the glenosphere or glenoid baseplate, as is required by the particular patient's anatomy or fracture type/location.

FIG. 17 shows an anterior view of an embodiment of a modular fracture plate that secures to the rTSA glenoid component to help reconstruct a fractured scapula while also achieving implant fixation, shown here on the acromion to reconstruct a fractured acromion as this is a common rTSA complication.

FIG. 18 shows an on face view of an embodiment of a modular fracture plate that secures to the rTSA glenoid component to help reconstruct a fractured scapula while also achieving implant fixation, shown here on the acromion to reconstruct a fractured acromion as this is a common rTSA complication.

FIG. 19 shows a posterior-oblique view of an embodiment of a modular fracture plate that secures to the rTSA glenoid component to help reconstruct a fractured scapula while also achieving implant fixation, shown here on the acromion to reconstruct a fractured acromion as this is a common rTSA complication.

Modular rTSA Muscle Augment Attachments to Provide Improved rTSA Joint Biomechanics, Particularly Posterior Rotator Cuff Efficiency by Changing the Line of Action of the Infraspinatus and Teres Minor Muscles to Improve Their Muscle Tension, and Also Increase Each Muscle's External Rotation and Abduction Moment Arm Lengths, According to Some Embodiments of the Present Invention In one embodiment, the modular attachment is a muscle augment configured to improve rTSA joint biomechanics in a patient in need thereof.

Figure 20:
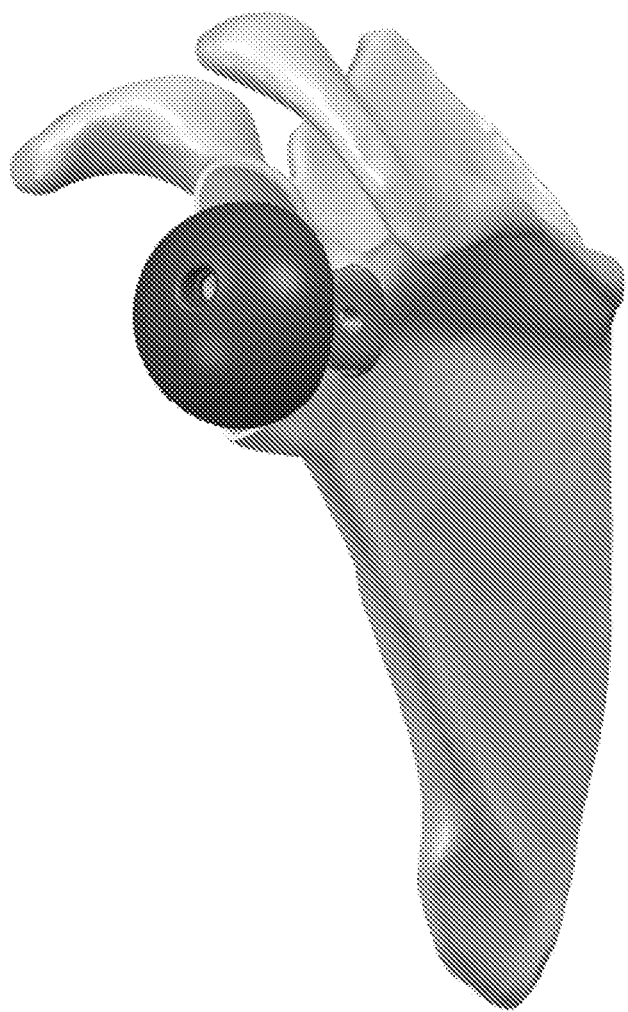
FIG. 20 shows a modular attachment according to some aspects of the present invention.
Figure 21:
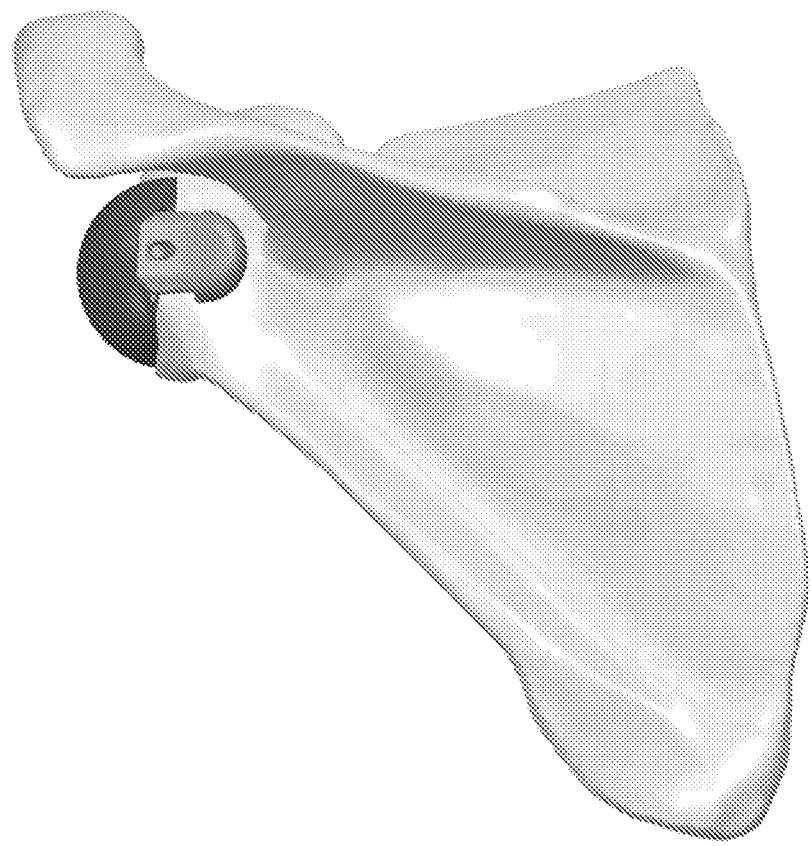
FIG. 21 shows another view of a modular attachment according to some aspects of the present invention.
Figure 22:
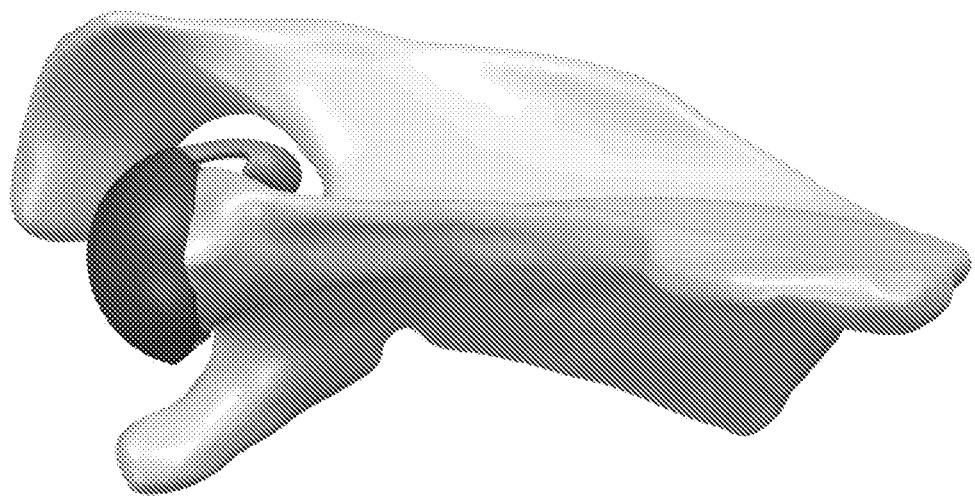
FIG. 22 shows another view of a modular attachment according to some aspects of the present invention.

FIGS. 20 to 22 depict multiple modular rTSA muscle augments which could attach to the back of the glenosphere or to the front or back of the baseplate to improve muscle biomechanics with rTSA by improving rotator cuff muscle tension and/or changing the line of action of the rotator cuff muscles to increase its rotation and abduction moment arm lengths. The images below specifically depict the use of these muscle augments on the posterior scapula to specifically improve the biomechanics of the posterior rotator cuff muscles (infraspinatus and teres minor).

In some embodiments, it is advantageous with rTSA to improve the function of the posterior rotator cuff as external rotation is limited with all commercially available rTSA designs. Additionally, in some embodiments, if a patient has limited external rotation musculature, improving the efficiency of the posterior cuff muscles may make it so the surgeon is not required to perform any additional muscle transfers.

In some embodiments, the muscle augment is utilized on the posterior scapula to posteriorly translate the line of action of the infraspinatus and teres minor muscles to strategically increase these muscles external rotation moment arms, in order to make them more efficient in generating an external rotation torque (thereby, decreasing the force required to be generated by each muscle to produce the external rotation motion/torque).

Additionally, the line of action of each muscle should also be superiorly shifted relative to its normal position with rTSA so that its line of action is more superior in position relative to the joint center of rotation, a more superior line of action relative to the joint center of rotation would permit each muscle to have a larger abduction moment arm and thereby, aid the deltoid in elevating the arm as opposed to acting against the deltoid as it does when the line of action is below the joint center of rotation.

In some embodiments, it is important that the position of the muscle augment be placed as medial as possible to avoid any rTSA prosthesis impingement, which could reduce range of motion or result in instability.

In some embodiments the muscle augments can be placed on the anterior or superior scapula as well to improve the moment arms of the subscapularis or supraspinatus, respectively.

Regardless of the location of the muscle augment, it is important to note that in some embodiments, the augment is highly polished and has a spherical articulation to prevent any muscle abrasion as the muscle glides over the augment during contraction and also as it is stretched over the different ranges of motions.

Alternatively, these modular muscle augments may be provided in various shapes, sizes, and thicknesses (which could be either uniform or nonuniform in curvature so that the muscle/muscle moment arms change as a cam with varying rotational positions. These modular muscle augments could accept locking, compression, or compression locking screws (and/or other fixation devices, such as sutures or wires) so that it can be secured directly to scapula. Additionally, the muscle augment may be modularly attached to the baseplate and/or glenosphere using various methods, including tapers, clips, screws, or other clasping mechanisms to secure the augment.

FIG. 20 shows a posterior-oblique view of an embodiment of a modular muscle augment that secures to the rTSA component to alter the posterior cuff muscle line of action in order to increase its external moment arm.

FIG. 21 shows a posterior view of an embodiment of a modular muscle augment that secures to the rTSA component to alter the posterior cuff muscle line of action in order to increase its external moment arm.

FIG. 22 shows an inferior view of an embodiment of a modular muscle augment that secures to the rTSA component to alter the posterior cuff muscle line of action in order to increase its external moment arm.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated). All publications and other references mentioned herein are incorporated by reference in their entirety, as if each individual publication or reference were specifically and individually indicated to be incorporated by reference.

Publications and references cited herein are not admitted to be prior art.

What is claimed is:

1. A kit, comprising:
   a prosthesis including
      a glenosphere having a first side, a second side opposite the first side, an articular surface on the first side, a hollowed out portion on the second side, and a perimeter at an intersection of the first and second sides;
      a glenoid plate including a body portion and a stem portion, the body portion having a first side and a second side and being operatively connected to the hollowed out portion of the glenosphere such that the first side of the body portion faces the glenosphere, the stem portion extending from the second side of the body portion and being configured to be fixed to a glenoid of a patient; and
      a plurality of accessory fixation points, each of the plurality of accessory fixation points being configured to receive an accessory fixed thereto through use of a fastening mechanism,
         wherein each of the plurality of accessory fixation points is located either on the glenosphere or on the glenoid plate,
         wherein the plurality of accessory fixation points are (a) positioned on the second side of the glenosphere and arranged around a perimeter of the second side of the glenosphere, (b) located on the body portion of the glenoid plate and arranged around the stem portion of the glenoid plate, or (c) a combination thereof, and
         wherein at least one of the plurality of accessory fixation points is positioned on the glenosphere; and
   a plurality of accessories, each of the accessories being configured to be secured to a selected one of the accessory fixation points of the prosthesis,
      wherein at least one of the accessories has a first end and a second end, the first end being configured to be secured to the selected one of the accessory fixation points of the prosthesis through use of a fastening mechanism, the second end being configured to be attached to bone of a patient at a location outside the perimeter of the glenosphere, and
      wherein at least one of the plurality of accessories is a plate that is bendable either fully or at predefined regions, whereby the at least one of the plurality of accessories can be shaped intraoperatively to meet anatomic or morphological needs of a patient.

2. The kit of claim 1, wherein at least one of the plurality of accessories is configured to facilitate fixation of the prosthesis to the scapula.

3. The kit of claim 1, wherein at least one of the plurality of accessories has a first end that is configured to be attached to the selected one of the accessory fixation points of the prosthesis and a second end that is configured to be attached to the scapula.

4. The kit of claim 3, wherein the second end of the at least one of the plurality of accessories is configured to be attached to one of an anterior portion of the scapula, a posterior portion of the scapula, an acromion of the scapula, or a scapular spine.

5. The kit of claim 3, wherein the first end of the at least one of the plurality of accessories is configured to be attached to a selected two of the accessory fixation points of the prosthesis.

6. The kit of claim 1, wherein at least one of the plurality of accessories has a shape corresponding to a shape of a portion of the scapula.

7. The kit of claim 6, wherein the at least one of the plurality of accessories is configured to contain a bone graft.

8. The kit of claim 1, wherein at least one of the plurality of accessories is one of contoured or bendable.

9. The kit of claim 1, wherein at least one of the plurality of accessories is configured to be positioned between glenoid plate and the glenoid of the patient so as to translate a joint line in a lateral direction.

10. The kit of claim 1, wherein at least one of the plurality of accessories includes a muscle augment.

11. The kit of claim 10, wherein the muscle augment is configured to translate a line of action so as to increase a moment arm of one of an infraspinatus muscle, a teres minor muscle, a subscapularis muscle, or a supraspinatus muscle.

12. The kit of claim 1, wherein at least some of the fixation points are arrayed around the hollowed out portion on the second side of the glenosphere.

13. The kit of claim 1, wherein at least some of the fixation points extend through the glenoid plate from the first side of the body portion of the glenoid plate to the second side of the body portion of the glenoid plate.

14. The kit of claim 13, wherein a plurality of slots are formed in the second side of the glenosphere and extend from the perimeter to the hollowed-out portion so as to enable access to the fixation points at the second side of the body portion of the glenoid plate.

15. The kit of claim 1, wherein some of the fixation points are arrayed around the hollowed out portion on the second side of the glenosphere, and wherein some of the fixation points extend through the glenoid plate from the first side of the body portion of the glenoid plate to the second side of the body portion of the glenoid plate.

16. The kit of claim 1, wherein the fastening mechanism includes at least one of a taper, a clip, or a screw.

* * * * *